(12) United States Patent
Vlachomitrou et al.

(10) Patent No.: US 9,066,687 B2
(45) Date of Patent: Jun. 30, 2015

(54) PANORAMIC DENTAL X-RAY UNIT

(71) Applicant: TROPHY, Marne la Valle, Cedex (FR)

(72) Inventors: Anna-Sesilia Vlachomitrou, Paris (FR); Sylvie Bothorel, Paris (FR); Jean-Marc Inglese, Bussy-Saint-Georges (FR)

(73) Assignee: Carestream Health, Inc., Rochester, NY (US)

( * ) Notice: Subject to any disclaimer, the term of this patent is extended or adjusted under 35 U.S.C. 154(b) by 170 days.

(21) Appl. No.: 13/677,693

(22) Filed: Nov. 15, 2012

(65) Prior Publication Data

US 2013/0129040 A1    May 23, 2013

(30) Foreign Application Priority Data

Nov. 17, 2011 (FR) ..................... 11 60467

(51) Int. Cl.
*A61B 6/14* (2006.01)
*A61B 6/00* (2006.01)

(52) U.S. Cl.
CPC ... *A61B 6/14* (2013.01); *A61B 6/52* (2013.01); *A61B 6/5205* (2013.01)

(58) Field of Classification Search
USPC .......... 378/1, 38, 39, 40, 167, 168, 195, 196, 378/197, 198
See application file for complete search history.

(56) References Cited

U.S. PATENT DOCUMENTS

| | | |
|---|---|---|
| 5,677,940 A | 10/1997 | Suzuki et al. |
| 6,466,641 B1 | 10/2002 | Virta et al. |
| 7,336,763 B2 | 2/2008 | Spartiotis et al. |
| 2004/0000630 A1 | 1/2004 | Spartiotis et al. |
| 2006/0203959 A1 | 9/2006 | Spartiotis et al. |
| 2010/0074403 A1 | 3/2010 | Inglese et al. |
| 2011/0142199 A1 | 6/2011 | Kantor et al. |

FOREIGN PATENT DOCUMENTS

EP    2 156 791    2/2010

OTHER PUBLICATIONS

European Search Report mailed Jan. 3, 2013 for European Patent Application No. 12007734.2, 2 pages.

*Primary Examiner* — Nicole Ippolito
*Assistant Examiner* — Hanway Chang (57) ABSTRACT

A panoramic dental x-ray unit. The unit includes a support rotating about an axis and carrying, in the opposite position, an x-ray source and detector which move following a predetermined trajectory. The unit further includes means for acquiring images of the dental arch of a patient corresponding to the positions of the detector and of the source with respect to the dental arch. There is also provided means for reconstruction of a two portions of a panoramic image corresponding respectively to two disconnected portions of the dental arch, the reconstruction being performed from certain acquired images which each contain at least one piece of information concerning the two disconnected portions of the dental arch.

18 Claims, 12 Drawing Sheets

PANORAMIC DENTAL X-RAY UNIT

CROSS REFERENCE TO RELATED APPLICATIONS

This application claims priority to FR 1160467 entitled "APPAREIL DE RADIOLOGIE DENTAIRE PANORAMIQUE", filed Nov. 17, 2011 to Vlachomitrou et al.

FIELD OF THE INVENTION

This invention concerns a dental x-ray apparatus and a method of usage of this dental x-ray unit.

In the field of dental radiology, panoramic x-ray machines are known, consisting of an x-ray source which transmits through a vertical collimation slot and an x-ray detector, located facing each other and installed at both ends of a rotary arm. This rotary arm is supported by a horizontal arm fixed to a vertical column.

SUMMARY

Before the taking the x-ray, the patient is positioned either standing or sitting between the x-ray source and the detector and the vertical position of the horizontal arm supporting the rotary arm is adjusted so that the x-ray beam irradiates at least the one of the patient's jaws (either the upper or lower jaw). While taking the panoramic x-ray, the rotary arm performs a combined movement of rotation about its axis and by translation through moving its axis, in such a way that the x-ray source and detector each perform a predetermined trajectory around the patient's head.

A panoramic dental x-ray is developed of the patient's jaw. It is composed of a succession of images each representing only a small part of the jaw, obtained at different angular positions of the rotary arm, and are connected to each other so as to obtain a representation of the entire dental arch.

Essentially, two basic conditions must be met to obtain a panoramic x-ray of good quality. First, the direction of the x-ray beam must, at every moment, be as close to perpendicular as possible to the portion of the dental arch irradiated. Therefore, for each image representing a portion of dental arch, the axis of the rotary arm must be placed so that the x-ray beam irradiates the dental arch at normal incidence.

If not, the panoramic x-ray may show overlapping teeth that do not exist in reality. To this end, the axis of rotation of the rotary arm must be moved along a predetermined trajectory during the production of the panoramic x-ray.

Shifting the axis can be achieved by a pair of servo motors for movement in the horizontal plane. Movement of the axis along a single straight line is a more economical solution as it requires the use of only one servo motor and nevertheless allows the production of panoramic x-rays of a satisfactory quality. An alternative solution to linear motion is the combination of two rotational movements. Document US 2011/0142199 proposes using a horizontal rotation of the arm with respect to the vertical column coupled to a linear movement of the rotary arm relative to the horizontal arm. Document U.S. Pat. No. 6,466,641 proposes the combination of two rotary movements involving an intermediate arm placed between the horizontal arm and the rotary arm.

The trajectory of the axis while taking the panoramic x-ray is predefined and controlled by a microprocessor. Some dental panoramic x-ray machines offer several predefined trajectories tailored for example to the jaws of children, V or U shaped jaws. Document US 2010/0074403 also proposes a preliminary radiological examination of the bite plane, in this case, a three-dimensional x-ray ("Computed Tomography" according to English terminology) to precisely locate the upper and lower dental arches. The information relative to location is then used to determine the trajectory of the rotary axis while taking the panoramic x-ray.

The second condition to be satisfied for a panoramic x-ray of good quality is the correct position of the focal spot. As the x-ray source and detector are located on either side of the patient, different bone structures are superimposed on unreconstructed x-rays images (the incisors with the spine, the right and left molars . . . ).

The tomography consists of superimposing images of the same area of interest, these images being taken at different angles of the x-ray beam with respect to the area of interest. This technique allows for a depth of field the position and breadth of which depend upon the x-ray machine's predetermined kinematic parameters, in this case, the position of the axis, the velocity profile of the x-ray source and detector and the width of the collimator slot installed in front of the x-ray source. After pixel-to-pixel stacking of the x-rays, bony structures located outside the focal spot are fuzzy and translate into horizontal strips (streaking blur or motion blur) which do not disturb the display of the bony structures within the focal spot.

The disadvantage of this technique is that the preset depth of field does not necessarily match the position of the area of interest, in this case, the patient's teeth, even when multiple axis trajectories are predefined.

The principle of tomosynthesis, for example, as described in document U.S. Pat. No. 5,677,940, makes it possible to solve this problem by choosing an area other than the predetermined focal spot and adjusting the position of the focal spot of the dental arch of each patient. With CMOS or TFT x-ray detectors, pixel shifting is carried out first on each image of several successive images of the portion of the dental arch, the extent of this shift being selected so that the bone structure of interest will be located, after the pixel shift, in the same position in all of the x-rays. After pixel-to-pixel stacking of all the x-rays, a tomographic shot is obtained upon which the bony structures of interest are located in the focal zone and the other bony structures are blurred and do not result in horizontal bands.

Since the pixel shifting is made afterwards, it is free to obtain by this technique, with only a single exposure of the patient to x-rays, several panoramic x-rays along several different focal spots associated with several ranges of pixel shift. For example, U.S. Pat. No. 7,336,763 teaches to first obtain a panoramic x-ray along a predefined focal spot corresponding to a first predefined pixel shift range or a lack of shifting, followed by calculating a second panoramic x-ray according to a second focal spot, at least along one portion of the dental arch, corresponding to a second pixel shift range. The second shift range is set such that the portion of the dental arch is considered to have an optimal focus. This technique, similar to an auto-focus software, makes it possible to automatically adapt the focal spot to all dental arches.

Practitioners are always seeking to limit patient exposure to ionizing radiation. Tomosynthesis, by allowing an adjustment of the position of the focal spot, eliminates the need to repeat the x-ray examination in the case where the patient has been incorrectly positioned or because the choice of the predefined trajectory of the axis of rotation from among a plurality of predefined trajectories was not adequate. Thus, tomosynthesis participates in the reducing patient exposure to ionizing radiation.

In view of the foregoing, it would be interesting to further exploit the potential of the tomosynthesis technique to further reduce the dose to be received by a patient to obtain a panoramic x-ray.

This invention utilizes, on the one hand, the ability of tomosynthesis to obtain a plurality of panoramic x-rays corresponding to a plurality of focal spots from a single x-ray exposure, and secondly, the fact that some of the images used for reconstruction of the panoramic x-ray each having information relating to the two disconnected portions of the dental arch.

This invention thus proposes a panoramic dental x-ray unit comprising:

a support which is able to rotate about an axis, an x-ray source installed at one end of the support and in front of which is placed a collimation slot so as to produce an elongated x-ray beam, an x-ray detector of elongated shape, installed at an end opposite of the support, placed towards the source and intended to receive the x-rays having traversed the patient's dental arch placed between the source and the detector, means for controlling the movement of the support so that the source and the detector follow a predetermined trajectory, means for acquiring several images of the patient's dental arch corresponding to a plurality of positions of the detector and the source with respect to the dental arch, means of reconstructing a panoramic image of at least one portion of the patient's dental arch from said plurality of images, characterized in that the means to reconstruct a panoramic image comprises the means to reconstruct two portions of the image corresponding respectively to two disconnected portions of the dental arch from at least some of the acquired images each of which contain at least one piece of information concerning the two disconnected portions of the dental arch.

Thus, the two disconnected portions of the dental arch are reconstructed ("viewed" by the x-ray beam as one behind the other) from the images acquired by the unit during the movement of the x-ray source and detector over a single angular range of movement. During the acquisition of a single image, information about two disconnected portions of the dental arch are obtained and will be utilized to reconstruct these two portions without the need to acquire more images on another angular range of movement. The angular range of movement is limited and is for example, lower than 180° and in particular lower than 90°. The angular range of movement is adjusted in order to avoid the possibility of overlapping teeth in the panoramic x-ray.

This overlap is obtained when the x-ray beam is not perpendicular to the teeth.

Such a device allows taking a panoramic x-ray by exposing the patient to a lower dose because it dispenses with the need (of the prior art) to acquire certain images.

In particular, the x-ray detector comprising a matrix of pixels, the reconstruction of the two portions of the panoramic image from images which each contain information relating to these portions, is carried out by shifting and stacking pixels, the shifting being of a different range for the reconstruction of each of the two portions, in order to obtain a focal spot adapted to each portion.

According to one possible characteristic, the means for reconstruction is capable of making corrections to standardize the scale of the two disconnected portions of the dental arch.

In one possible characteristic of the invention, the axis of the rotary arm of the unit can move along a straight line segment located along the anterior-posterior direction relative to the patient during the acquisition of the plurality of images.

This arrangement makes it possible to limit the number of servo motors to two, the first for rotating the rotary arm and the second for translation along the line segment. This arrangement is simple and economical.

More specifically, the straight line segment may be located in the mid-sagittal plane. This plane is an imaginary plane that intersects the body vertically into two equal parts.

According to one possible characteristic, the axis of the rotary arm of the unit can move in several horizontal directions while acquiring the plurality of images. This arrangement, more expensive than the first, ensures better positioning of the axis, and thus the x-ray source and detector, with respect to the patient's dental arch, to have better orthogonality (more accurate orthogonality) of the x-ray beam with regard to the segment or portion of the irradiated dental arch.

According to one possible characteristic, the images, each containing information relating to the two disconnected portions of the dental arch, are acquired during a pure rotational movement of the rotary arm. "Pure" rotation is understood to mean a movement that has no other geometric/motion transformation than one or more rotations. This mode of acquisition of this type of images makes it possible to have, after the reconstruction of the panoramic image, the same conditions of x-ray beam orthogonality with the left and right sides of the dental arch, in particular, the molars and the bicuspids, and close to the condyles.

According to one possible characteristic, the images, each containing information relating to the two disconnected portions of the dental arch, are acquired during a combined translational and rotational movement of the rotary arm.

According to one possible characteristic, the trajectory of the x-ray source is not symmetrical with respect to the antero-posterior direction relative to the patient. This is a consequence of the fact that the invention makes the acquisition of certain images unnecessary for the reconstruction of panoramic x-ray. This asymmetry reflects the fact that, thanks to the invention, certain parts of the patient's head are not irradiated twice, as was done in the prior art.

It should be mentioned that the trajectory of the x-ray detector may not be symmetrical with respect to this same direction.

The invention further has for its object a method of obtaining a panoramic dental image involving a panoramic dental x-ray unit comprising:

a support which is able to rotate about an axis, an x-ray source installed at one end of rotary arm and in front of which is placed a vertical collimation slot so as to produce an elongated x-ray beam, an x-ray detector of elongated shape, installed at an end opposite of the support, placed towards the source and intended to receive the x-rays having traversed the patient's dental arch placed between the source and the detector, the method comprising:

control for the movement of the support so that the x-ray source and detector follow a predetermined trajectory, acquisition of several x-ray images of the patient's dental arch corresponding to a plurality of positions of the x-ray detector and source with respect to the dental arch, reconstruction of a panoramic image of at least one portion of the patient's dental arch from said plurality of images, characterized in that the reconstruction of a panoramic image comprising the reconstruction of two portions of the image corresponding respectively to two disconnected portions of the dental arch from at least some of the acquired images each of which contain at least one piece of information concerning the two disconnected portions of the dental arch.

In accordance with the possible characteristics of the method alone or in combination:

the x-ray detector comprising a pixel matrix, the reconstruction of the two portions of the panoramic image is performed by shifting and stacking of pixels, the shift being of a different range to reconstruct each of the two portions.

reconstruction comprises carrying out corrections for the standardization of the scale of the two disconnected portions of the dental arch.

the axis moves along a straight line segment while acquiring the plurality of images located following the antero-posterior direction relative to the patient and, for example, more specifically, on the mid-sagittal plane.

the axis moves in several directions while acquiring the plurality of images.

the images, each containing information relating to the two disconnected portions of the dental arch, are acquired during a rotary movement of the support.

the images, each containing information relating to the two disconnected portions of the dental arch, are acquired during a combined translational and rotational movement of the support.

the trajectory of the x-ray source is not symmetrical with respect to the antero-posterior direction relative to the patient.

BRIEF DESCRIPTION OF THE DRAWINGS

The other characteristics and advantages of the invention will be mentioned in the following description, given only as a non-restrictive example and made in reference to the attached drawings, in which.

DETAILED DESCRIPTION OF EXEMPLARY EMBODIMENTS

Figure 1A:
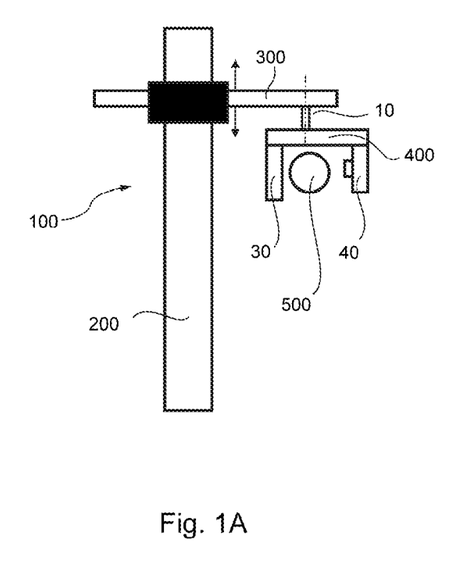
FIG. 1A is a general diagrammatic view of the x-ray unit in accordance with the invention.

As shown in FIG. 1A, a dental x-ray unit (100) according to the invention is a panoramic type device. This device makes it possible to produce panoramic x-rays of an object such as a dental arch. The unit comprises a vertical column (200) which is mounted on a horizontal arm (300), whose vertical position can be adjusted and supporting a movable support such as a rotary arm (400). An x-ray source (40) is placed on one end of the rotary arm (400) and an x-ray detector (30), for example, pixel matrix, with a size of 64×1344 pixels, is placed at an opposite end of the rotary arm, such that the x-ray source (40) and the x-ray detector (30) are always opposite each other and that the patient (500) is always located between the two. Thus, the detector receives the x-ray beam having passed through the patient. The rotary arm (400) is integrated with an axle (10) carried by the horizontal arm (300) and movable relative to the horizontal arm.

Figure 2A:
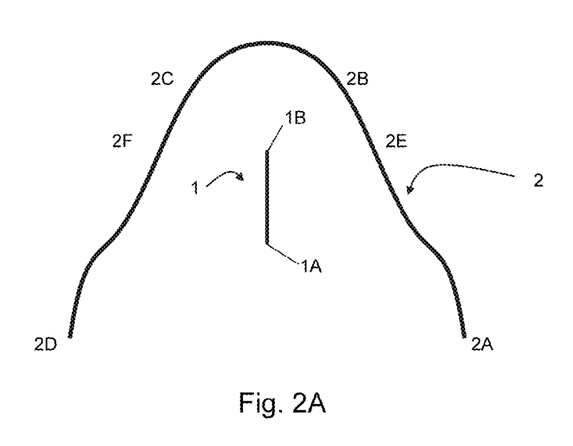
FIG. 2A is a general schematic view showing the relative position of a patient's dental arch and of the trajectory of the rotary arm's axis of rotation in the mid-sagittal plane, according to an embodiment of the invention.

The rotation, or more generally the shift of the axis (10) carries the rotary arm into rotation or following a more general movement such as translation or following a combined translational and rotational movement, or following another movement. The means for controlling the movement of the support or arm (400) are provided so that the x-ray source and detector each moves along a predetermined trajectory, for example a flat trajectory. In a preferred embodiment of the invention, the axis is controlled by a pair of servo motors, one of the two servo motors providing translational movement of the axis (10) in a given direction, preferably in the antero-posterior direction relative to the patient (as shown in FIG. 2A by the line segment 1A-1B that 1A indicates, the posterior end and 1B the anterior end), the other servo motor ensures the rotation of the axis (10). This invention can be fitted to an imaging unit wherein the axis is moved differently, as follows, first, a rotary movement of the axis and, secondly, the movement of the axis in the horizontal plane (inside the area shown within the dotted lines in FIG. 2B) for example by combining two translations. Other kinematic movement of the axis in the horizontal plane is also possible such as a combination of two rotations or one rotation, and a translation. Documents US 2011/0142199 and U.S. Pat. No. 6,466,641 describe this type of kinematics.

Figure 2B:
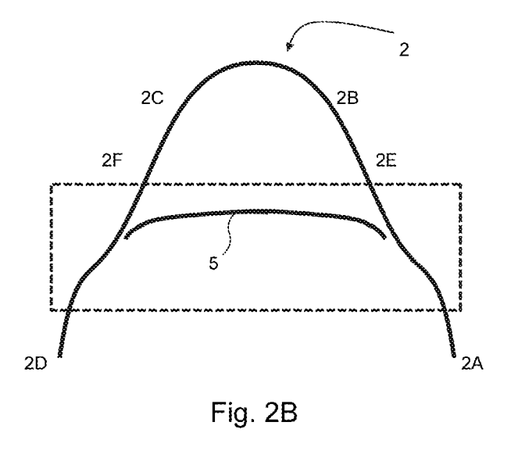
FIG. 2B is a general schematic view showing the relative position of a patient's dental arch the trajectory of the rotary arm's axis of rotation according to an embodiment of the invention involving two horizontal translations.

The trajectory (5) in two dimensions shown in FIG. 2B presents a very good compromise between the simplicity of the kinematics of movement and the condition of orthogonality of the x-ray beam with respect to the dental arch.

Note that the number of servo motors is adapted to the movement(s) to be performed. Thus, three servo motors are, for example, used to perform one movement of rotation and two different translational movements.

In panoramic imaging, the x-ray beam is collimated to the output of the x-ray source through, for example, a vertical slot, which consequently gives a general pyramidal shape, which, seen from above, takes the form of a triangle.

Figure 3:
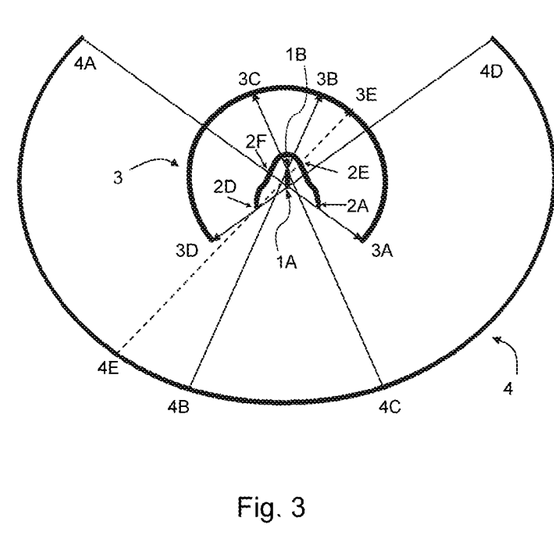
FIG. 3 is a general schematic view showing the relative positions of a patient's dental arch, of the trajectory of the rotary arm's axis of rotation, of the x-ray source and detector at different stages of acquiring a panoramic x-ray according to a known mode of acquisition of the prior art.

Throughout the description and the Figures, the x-ray beams represented in top view, however, are voluntarily illustrated schematically by a straight line for simplicity and clarity. With reference to FIG. 3, the kinematics will now be described of the movement of the assembly consisting of the axis (10), of the x-ray source (40) and detector (30) to produce a panoramic shot according to the prior art, in order to better understand the invention.

Before starting the image acquisition, the axis (10) is positioned at the rear end (1A) of the straight line segment, the x-ray source (40) at the point (4A) of its trajectory (4), and the x-ray detector (30) is located at the point (3A) of its trajectory (3), in this case, behind the right ear of the patient, as shown in FIG. 3.

The x-ray source (40) is then turned on and the x-ray beam irradiates in a pyramid form the jaw (2) of the patient. Referring to FIG. 3, the axis moves from its point of departure (1A) to point 1B. This translational motion is combined with a rotary motion of the arm around the axis. This rotation is essential to the implementation of tomography. The rotation of the rotary arm is at a variable speed; speed variations are used to optimize the quality of the shot.

Thus, as shown in FIG. 3, the x-ray source (40) supported by one end of the rotary arm moves from point 4A to point 4B of the trajectory (4). The x-ray detector (30) moves, meanwhile, from point 3A to the point 3B of the trajectory (3).

When the axis (10) has reached the end (1B) of its trajectory (1), the x-ray source (40) has reached point 4B and the x-ray detector (30) reaches point 3B. The axis (10) is now stationary in translation and then it starts to turn on itself, causing the rotary arm to move in a pure rotational motion. The x-ray source (40) moves in a circular arc from point 4B to point 4C and the x-ray detector (30) moves, in turn, from point 3B to point 3C. Note that the angular step between two successive x-ray shots is smaller on the 3B3C area (incisors) than on the rest of the angular area scanned by the x-rays (with reference to FIGS. 3 and 4A).

The axis (10) then makes its way back by moving from point 1B to point 1A. The x-ray source then moves from point 4C to 4D and the x-ray detector from point 3C to point 3D.

The kinematics of the axis (10), the x-ray source (40) and the x-ray detector (30) are symmetrical during the final part of taking the panoramic image and when the panoramic shot was begun. The inventors have found that using this technique known in the prior art, some parts of the dental arch (2) of the patient, in this case, the molars and premolars, and one part of the patient's head were irradiated twice, during the outward and return journey of the rotary axis between the two ends of its rectilinear trajectory (FIG. 3).

Figure 4A:
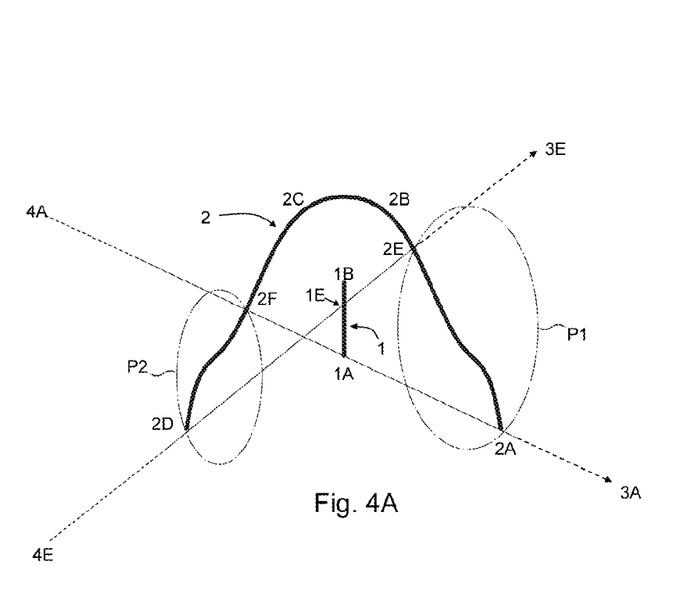
FIG. 4A is a schematic view showing the double irradiation of the left and right parts of the dental arch during the first acquisition phase of a panoramic x-ray.

Moreover, when the axis (10) is between positions 1A and 1E of its trajectory in FIG. 4A the x-ray source is located between positions 4A and 4E, the x-ray detector is between positions 3A and 3E, and the part or portion of the dental arch between points 2A and 2E is irradiated, as well as the part or portion of the dental arch between points 2D and 2F.

Thus, the inventors noticed that the images obtained for each of all successive positions of the x-ray source and from the x-ray detector contain information relating to the two disconnected portions of the dental arch respectively, between points 2A and 2E and points 2F and 2D (FIG. 4).

By processing the data acquired by shifting pixels and stacking images pixel by pixel and, in particular, by selecting two different values or ranges of pixel shift, the inventors have realized that it is possible to obtain two different focal planes, one corresponding to the dental arch portion between 2A and 2E and the other corresponding to the dental arch portion between 2D and 2F. This calculation uses the data collected by the x-ray detector (30) when the latter is located between the points 3A and 3E opposite the x-ray source (40), which itself is positioned between points 4A and 4E. The two disconnected portions of the dental arch (2A-2E) and (2F-2D) can be reconstructed from the same set of data acquired.

The angular sector covered by both the x-ray source and the x-ray detector to acquire this data is reduced compared to the prior art.

The end of the sequence of image acquisition in the prior art, in this case the part during which acquisition is performed in one portion of the return path of the axis from the point 1B to point 1A and, while the detector is to the left of the patient, becomes redundant with the acquisition portion achieved when the axis moves from point 1A to point 1B and the detector is to the right of the patient. By eliminating the need for one part of image acquisition as practiced in the prior art, the practitioner is able to reduce the dose to which the patient is exposed.

The radiology unit according to the invention is equipped with the means to implement the invention the principle of which has been stated above.

Figure 1B:
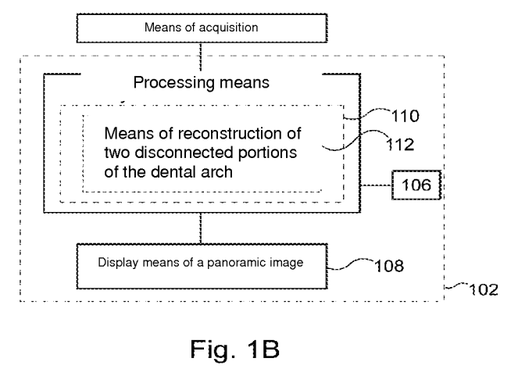
FIG. 1B is a schematic representation of devices forming part of the unit according to the invention.

For this purpose, the unit (100) comprises, as shown schematically in FIG. 1B, a processing and display unit (102) connected to the means for acquisition of images/data (30, 40). Generally speaking, the unit (102) comprises a means for data processing (104) (e.g., a processor), a means for storage or recording data (106) and means of display/data visualization/processed images (108) which for example, allow the display of one or more panoramic shots.

More specifically, the means for data processing (104) comprises the means for reconstruction of a panoramic dental image (110) of at least one portion of the dental arch of a patient from the images/data acquired by the means (30, 40).

These means (110) comprise the means to reconstruct two portions of panoramic images (112) corresponding to two disconnected portions of the dental arch (2A to 2E and 2F to 2D in FIG. 4A) and the means for reconstruction of a panoramic image corresponding to the remaining portion of the dental arch (2E to 2F in FIG. 4A).

The means for specific reconstruction (112) using images/data acquired (not necessarily all images/data acquired) when moving the x-ray source from position 4A to position 4E and of the x-ray detector, from position 3A to position 3E in FIG. 4A.

Each of the images/data thus acquired contains information on each of the two disconnected portions of the dental arch (2A to 2E and 2F to 2D) and which are surrounded respectively by the ovals P1 and P2.

Thus, during this movement on a limited angular range the images/data are acquired all at once which will be sufficient to reconstruct the two portions of the dental arch P1 and P2. The patient is thus exposed to a reduced x-ray dose compared to the prior art.

Note that a scale correction must be made for each portion or piece during the reconstruction of the two disconnected portions (2A to 2E and 2F-2D) and the remaining portion (2E to 2F) before the final reconstruction.

This scale correction is explained by the fact that the x-ray beam being tapered, the image of the object on the x-ray detector is amplified by a factor equal to the ratio of the distance between the x-ray source and the x-ray detector on the distance between the x-ray source and the object. This factor is clearly different for the two disconnected portions of the dental arch obtained during the same x-ray exposure.

The means for reconstruction (112) performs in this way a correction to standardize the scale.

Figure 4B:
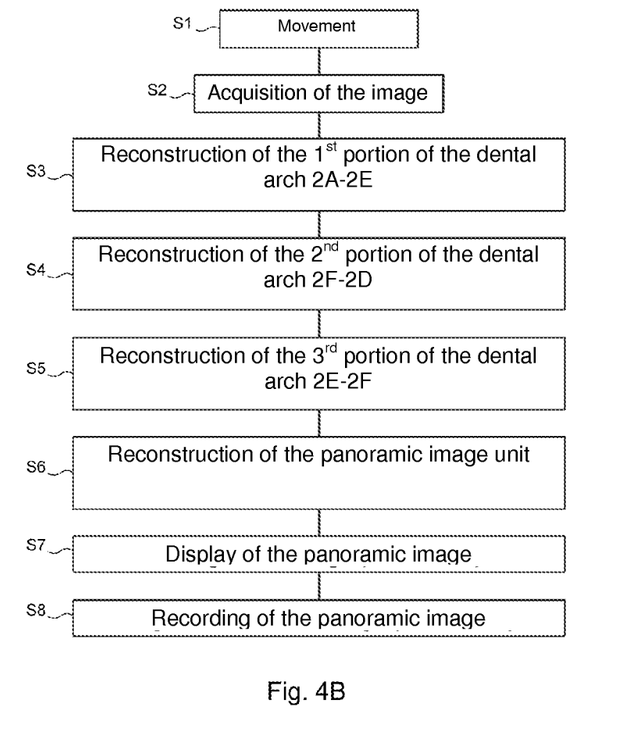
FIG. 4B shows a succession of the method's steps according to one embodiment of the invention.

FIG. 4B shows an algorithm that illustrates the method's steps for production of a panoramic dental image according to the invention.

Software stored in the unit (100) makes it possible, during its execution by the processing means (104) to implement the method of the invention.

The algorithm in FIG. 4B comprises a first step (S1) in which the support (400) carrying the x-ray source (40) and the x-ray detector (30) is moved in a plane perpendicular to the axis of rotation (10) of FIG. 1A.

More particularly, the movement of the support and therefore the x-ray source of the detector is controlled so that they each follow a predetermined path.

Figure 5:
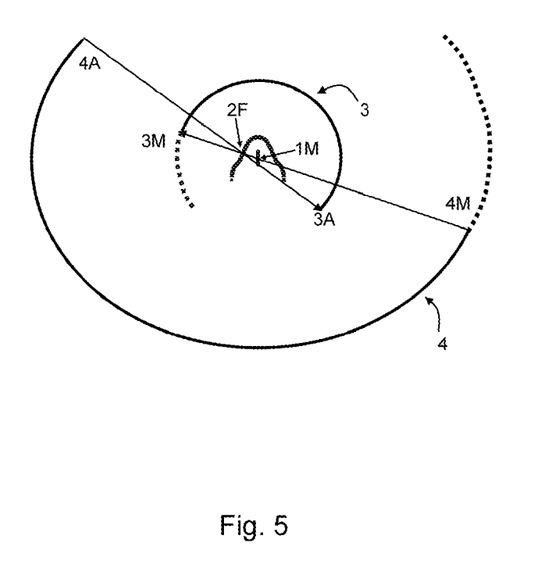
FIG. 5 is a general schematic view showing the relative positions of a patient's dental arch, of the trajectory of the rotary arm's axis of rotation, of the x-ray source and detector at different stages of acquiring a panoramic x-ray according to the invention.

FIG. 5, which will be described below, provides details on the movement of the axis (10) around which the support turns as well as on the trajectories of the x-ray source and detector.

The following step (S2) is the step to acquire images in which the x-ray detector (30) captures the radiation produced by the x-ray source and which has irradiated a part of the patient's jaw.

An image is acquired for each predetermined angular positions and selected for the source and the detector.

Note that steps S1 and S2 are carried out simultaneously as the image acquisition is executed during the movement of the source and detector.

During this movement the unit thus acquires several images of the patient's dental arch which correspond to a plurality of angular positions of the x-ray detector and source with respect to the dental arch.

The algorithm then comprises a step (S3) during which a first portion of the dental arch (2A-2E)(shown in FIG. 4A) is reconstructed from images captured by the source detector unit while the source moves from position 4A to position 4E and position 3A to 3E of the detector.

To obtain a focal plane adapted to this first portion of the dental arch, a range or an adapted pixel shift value (e.g., pixel shift) is selected prior to the stacking the pixels thus shifted.

This technique of shifting and stacking the pixels for the reconstruction of a dental image is known from the prior art and therefore will not be developed further.

The next step (S4) is established to undertake the reconstruction of a portion of the second dental arch (2F, 2D) shown in FIG. 4A, and which is disconnected from the first portion (2A-2E).

These two portions are scanned by the same x-ray beam when moving the source from its position 4A to its position 4E.

This reconstruction is performed from the images acquired by the source-detector unit when the source goes from position 4A to position 4E and the detector from position 3A to position 3E.

The focal plane is also moved and adapted to the second portion of the dental arch by translating the pixels from an adapted value or range before proceeding to stacking them.

Note that the position 2E defining one of the limits of the first portion of the dental arch varies according to the kinematics of the axis of rotation (10) of the unit.

The algorithm comprises a step following S5 which provides for the reconstruction of a third delimited portion of the dental arch by the positions 2E and 2F and which is adjacent to the first and second disconnected portions.

This third portion of the dental arch is reconstructed from images acquired by the source/detector unit during the movement of the source from position 4E of FIG. 4A to the position 4M of FIG. 5 and when the detector moves from position 3E of FIG. 4A to the position of 3M in FIG. 5.

Again, in order to move the focal plane of the image and to adapt it to the third portion of the dental arch, a range or shift value of pixels may be different from the first and the second value or shift range mentioned above and selected in a manner appropriate to the third portion of the dental arch.

The step following S6 is a reconstruction step of the entire panoramic image of the complete dental arch from the reconstruction of all three portions of the dental arch covered in steps S3, S4, and S5. This step includes a standardization of the scale as explained above.

Figure 6:
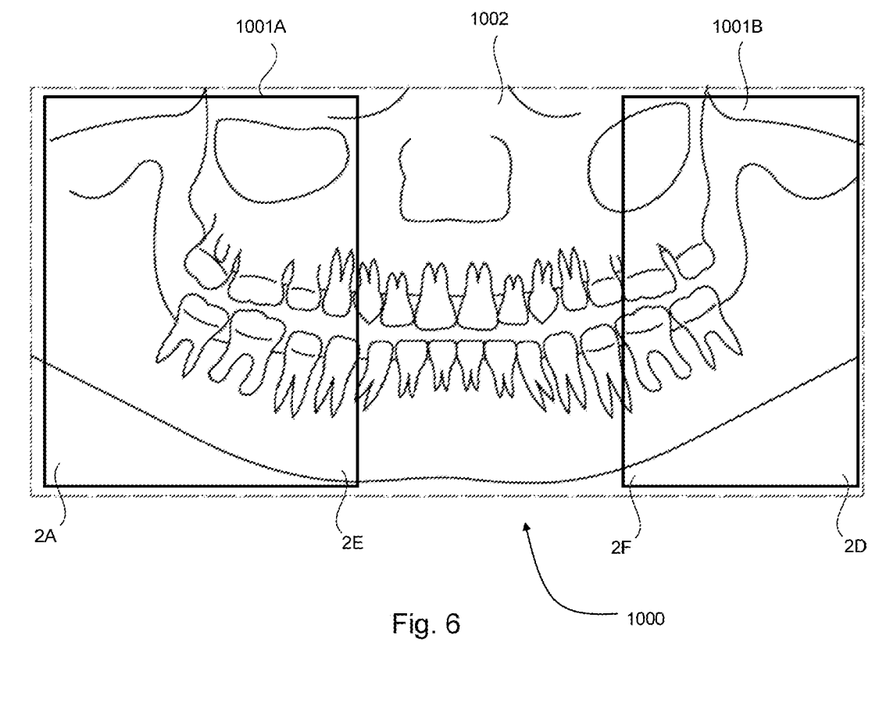
FIG. 6 is a schematic view of a panoramic x-ray obtained according to a first embodiment of the invention.

FIG. 6, which will be described below, shows the panoramic image thus reconstructed.

Note that each portion of dental arch just as the first portion and the second portion can themselves be decomposed into several segments of the dental arch, each segment being the object of a different pixel shift value or range to obtain a focal plane of the highest quality for a given portion of the dental arch.

The dental arch portion consisting of said plurality of segments is reconstructed using a plurality of pixel shift values or ranges.

At each disconnected portion of the dental arch is associated with a set of adapted pixel shift values or ranges.

The step following the S7 algorithm is provided to display the panoramic image reconstructed due to the means of display (108) of FIG. 1B.

The result of the display is also shown in FIG. 6 mentioned above.

The step following S8 is established in order to record a panoramic image reconstructed by the means of recording/storage (106).

FIG. 5 shows the kinematics of the unit consisting of the axis (10), of the x-ray source (40) and of the detector (30) according to the invention and which is implemented in step S1 of the algorithm of FIG. 4B. The axis (10) moves from point 1A to point 1B simultaneously performing a translational and rotational movement. Once it arrives at point 1B, it performs a pure rotational movement. Then, it returns towards point 1A by simultaneously carrying out a translational and a rotational movement. Finally, it stops on the trajectory back to point 1M, an intermediate point between the end points 1A and 1B. The detector (30) moves between points 3A and 3M and the source (40) between points 4A and 4M. Points 3M and 4M are the locations at which the x-ray detector (30) and the x-ray source (40) are when the x-ray beam irradiates the left side of the dental arch (2) at point 2F. Point 2F is the point irradiated by the x-ray beam at the start of the panoramic image acquisition when the x-ray source is positioned at point 4A, the axis (10) is at point 1A and the detector is at point 3A. The dotted lines shown illustrate each portion of the trajectory and thus the movement of the x-ray source and detector which they do not have to travel through thanks to the invention.

FIG. 6 shows a panoramic image (1000) with the two portions (1001A and 1001B) reconstructed from the same batch of images each comprising information relating to the two separate portions of an arch. It is found that, in this embodiment, the portion 1001B is less spatially extended than portion 1001A, which is also visible in FIG. 4A with portions 2A-2E and 2F-2D.

Kinematics as described herein is chosen so that the x-ray beam is as orthogonal as possible to the dental arch at any point on the portion between points 2A and 2E.

By contrast, these kinematics do not optimize the orthogonality of the x-ray beam with the dental arch on its portion between points 2F and 2D. Accordingly, it is expected that the quality of the panoramic realized according to the invention will be of better quality on its part (1001A) than on the part (1001B) where overlapping of teeth may be induced. In particular, there is a real loss of orthogonality near the left condyle, that is to say close to point 2D.

Figure 7A:
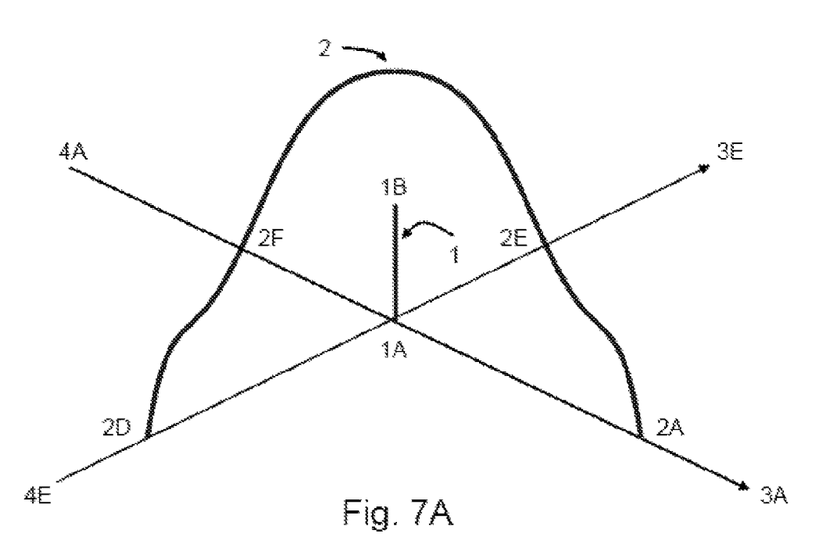
FIG. 7A is a schematic view showing the double irradiation of the left and right parts of the dental arch during the first acquisition phase of a panoramic x-ray according to a second embodiment of the invention.

To resolve this problem while maintaining the same mechanical system in which the axis (10) moves along a straight segment (1), it is sufficient that the rotating arm make a movement of pure rotation, when irradiating at least one part of the portion of the dental arch (2A-2E) (FIG. 7A). This rotary motion can be achieved when the axis (10) is still under point 1A or in another point between the ends (1A and 1B) of its trajectory. FIG. 7A shows the case where the axis (10), located at point 1A, performs a movement of pure rotation during irradiation of the entire dental arch portion from 2A to 2E. This type of a kinematic axis, also makes it possible through symmetry to have an image of the same quality on the right and on the left of the panoramic image. It also makes it possible to move point 2F of the dental arch forward with respect to the embodiment described with reference to FIG. 4. Thus, the kinematics can increase the length or spatial extension of the left portion of the dental arch which is irradiated at the same time as the right portion during the first part of the panoramic image capture. Point 2E is then moved to the back of the dental arch, towards the right condyle. Thus, the length of the dental arch (2A-2E) in FIG. 7A is reduced relative to that of FIG. 4A. The range of angular movement of the source-detector unit makes double irradiation possible which is wider than in the embodiment of FIG. 4, the total angular range necessary to achieve the panoramic shot is very narrow, in this case, 180°, as shown schematically in FIG. 7B, and the dose to the patient is further reduced.

The dotted lines shown on the trajectory of the x-ray source and of the detector also illustrate the portion of the trajectory that neither of them will have to traverse due to the invention.

Figure 7B:
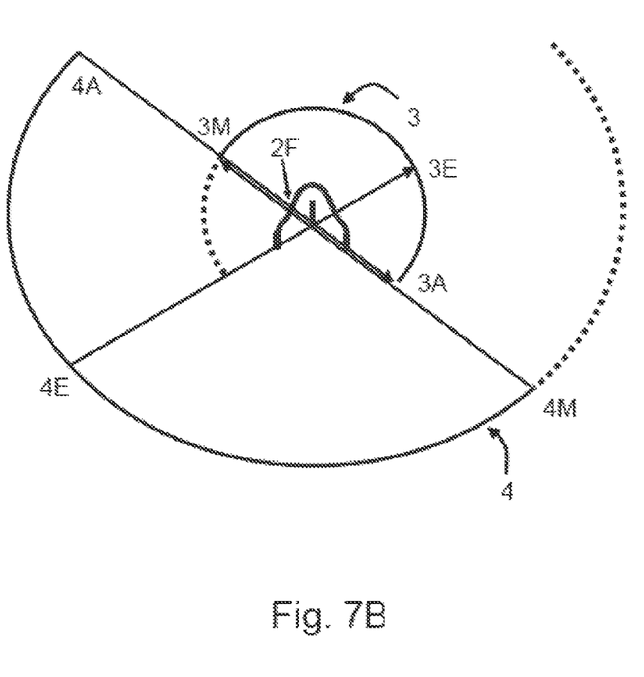
FIG. 7B is a schematic view showing the relative positions of a patient's dental arch, the rotary arm's axis of rotation, of the x-ray source and detector at different stages of the acquisition of a panoramic x-ray in the second embodiment of the invention.

It should be noted that in both embodiments of FIGS. 5 and 7B, the invention provides the information necessary to reconstruct the entire dental arch without the trajectory (3) of the detector (30) and the trajectory (4) of the x-ray source (40) being symmetrical with respect to the antero-posterior direction (segment 1 is aligned along this direction).

Figure 7C:
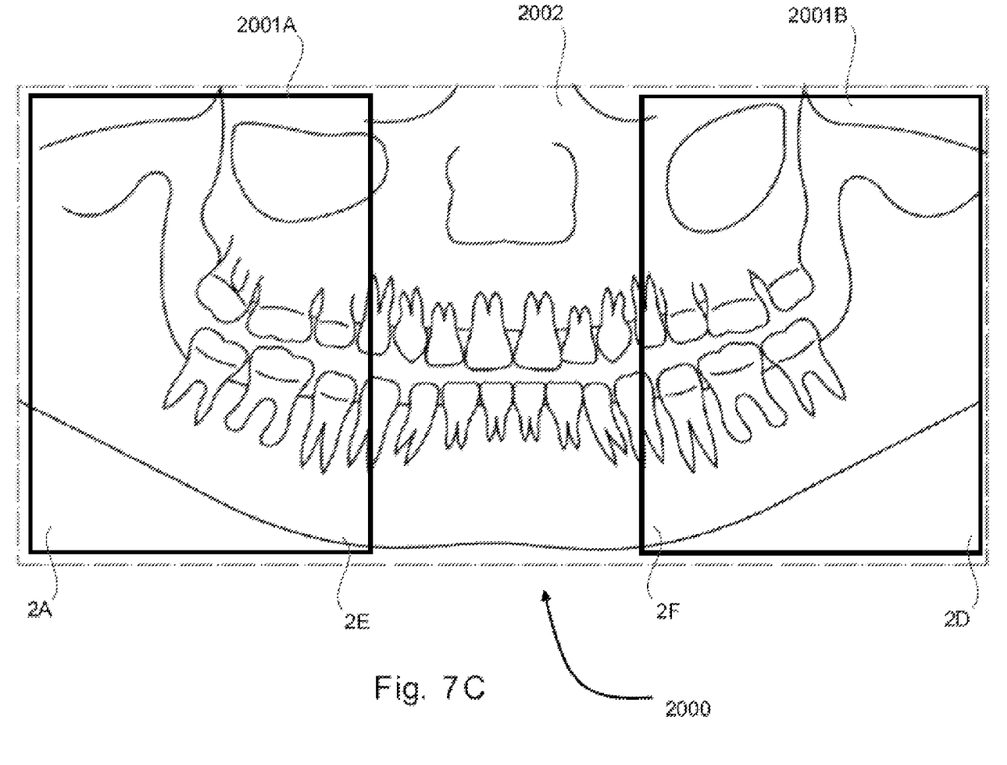
FIG. 7C is a schematic view of a panoramic x-ray obtained according to a second embodiment of the invention.

FIG. 7C shows a panoramic image (2000) with the two portions (2001A and 2001B) reconstructed from the same batch or plurality of images. It is found that, in this embodiment, the two portions (2001A and 2001B) have the same spatial length.

The invention has been described in the case of a movement of the rotary axis along a straight line segment. The invention may also be used, for example, in the case of a movement of the axis in two directions, by combining the two translational movements.

The invention may also be used in the case where only a rotational movement of the axis is authorized, the axis being associated with a single servo motor, ensuring its rotation.

The invention claimed is:

1. A panoramic dental x-ray device, comprising:
    a support able to rotate about an axis;
        an x-ray source installed at the support and in front of which is placed a collimation slot so as to produce an elongated X-ray beam;
        an x-ray detector of elongated shape, installed at the support, facing the source and intended to receive the X-rays having traversed a dental arch of a patient placed between the source and the detector;
        means for control of the support movement so that the source and the detector follow a predetermined trajectory;
        means for acquiring a plurality of images of the dental arch of a patient corresponding to a plurality of positions of the detector and of the source with respect to the dental arch; and
        means for reconstruction of a panoramic image of at least one portion of the patient's dental arch, from the plurality of images;
        wherein the means for reconstruction of the panoramic image comprises means to reconstruct two portions of the image corresponding respectively to two disconnected portions of the dental arch from at least some of the acquired images, which each contain at least one piece of information concerning the two disconnected portions of the dental arch.

2. The device according to claim 1, wherein the x-ray detector comprising a pixel matrix, and the reconstruction of the two portions of the panoramic image is performed by shifting and stacking of pixels, the shift being of a different range to reconstruct each of the two portions.

3. The device according to claim 1, wherein the means for reconstruction makes corrections to standardize the scale of the two disconnected portions of the dental arch.

4. The device according to claim 1, wherein the axis moves during the acquisition of the plurality of images along a straight line segment located in an antero-posterior direction relative to the patient.

5. The device according to claim 4, wherein the straight line segment is more specifically located in the mid-sagittal plane.

6. The device according to claim 1, wherein the axis moves in several directions while acquiring the plurality of images.

7. The device according to claim 1, wherein the images, each containing information relating to the two disconnected portions of the dental arch, are acquired during a rotary movement of the support.

8. The device according claim 1, wherein the images, each including information relating to the two disconnected portions of the dental arch, are acquired during a combined translational and rotational movement of the support.

9. The device according to claim 1, wherein the trajectory of the x-ray source is not symmetrical with respect to an antero-posterior direction relative to the patient.

10. A method for obtaining a panoramic image, comprising:
    providing a panoramic dental x-ray unit, comprising:
        a support able to rotate about an axis;
        an X-ray source installed at one side of a rotary arm and in front of which is placed a collimation slot so as to produce an elongated X-ray beam; and
        an x-ray detector of elongated shape, installed at an opposite side of the support, placed towards the source and intended to receive the X-rays having traversed a dental arch of a patient placed between the source and the detector;
    controlling the support movement so that the x-ray source and the detector follow a predetermined trajectory,
    acquiring a plurality of images of the dental arch of a patient corresponding to a plurality of positions of the detector and of the x-ray source with respect to the dental arch;
    reconstructing a panoramic image of at least one portion of the patient's dental arch, from the plurality of images, by reconstructing two portions of the image corresponding respectively to two disconnected portions of the dental arch from at least some of the acquired images, which each contain at least one piece of information concerning both of the two disconnected portions of the dental arch.

11. The method according to claim 10, wherein the x-ray detector comprises a pixel matrix, and the reconstructing of the two portions of the panoramic image is performed by shifting and stacking of pixels, the shift being of a different range to reconstruct each of the two portions.

12. The method according to claim 10, wherein the reconstructing of the two portions comprises carrying out corrections for the standardization of the scale of the two disconnected portions of the dental arch.

13. The method according to claim 10, further comprising moving the axis along a straight line segment during the acquisition of the plurality of images following an antero-posterior direction relative to the patient.

14. The method according to claim 13, wherein the straight line segment is more specifically located in the mid-sagittal plane.

15. The method according to claim 10, further comprising moving the axis in several directions while acquiring the plurality of images.

16. The method according to claim 10, wherein the plurality of images are acquired during a pure rotational movement of the support, each of the plurality of images including information relating to the two disconnected portions of the dental arch.

17. The method according to claim 10, wherein the plurality of images are acquired during a combined rotational and translational movement of the support, each of the plurality of images comprising information concerning the two disconnected portions of the dental arch.

18. The method according to claim 10, wherein the trajectory of the x-ray source is not symmetrical with respect to an antero-posterior direction relative to the patient.

\* \* \* \* \*